(12) United States Patent
Zarowski et al.

(10) Patent No.: US 12,017,070 B2
(45) Date of Patent: Jun. 25, 2024

(54) METHOD FOR DERIVING INFORMATION FOR FITTING A COCHLEAR IMPLANT

(71) Applicant: ENTIC RESEARCH AND TRAINING CENTER BV, Wilrijk (BE)

(72) Inventors: Andrzej Zarowski, Wilrijk (BE); Erwin Offeciers, Antwerp (BE); Joost Van Dinther, Wilrijk (BE); Marc Leblans, Kontich (BE); Fergio Sismono, Berchem (BE)

(73) Assignee: ENTIC RESEARCH AND TRAINING CENTER BV, Wilrijk (BE)

( * ) Notice: Subject to any disclaimer, the term of this patent is extended or adjusted under 35 U.S.C. 154(b) by 0 days.

(21) Appl. No.: 17/058,467

(22) PCT Filed: May 29, 2019

(86) PCT No.: PCT/EP2019/064041
§ 371 (c)(1),
(2) Date: Nov. 24, 2020

(87) PCT Pub. No.: WO2019/229162
PCT Pub. Date: Dec. 5, 2019

(65) Prior Publication Data
US 2021/0196954 A1   Jul. 1, 2021

Related U.S. Application Data

(60) Provisional application No. 62/678,375, filed on May 31, 2018.

(51) Int. Cl.
*A61N 1/36* (2006.01)
*A61N 1/05* (2006.01)

(52) U.S. Cl.
CPC ....... *A61N 1/36039* (2017.08); *A61N 1/0541* (2013.01)

(58) Field of Classification Search
CPC .............. A61N 1/36036–36039; A61N 1/0541
See application file for complete search history.

(56) References Cited

U.S. PATENT DOCUMENTS 7,835,804 B2 * 11/2010 Fridman ................ A61B 5/316
607/137
9,289,608 B2 * 3/2016 McDermott ....... A61N 1/36046
(Continued)

FOREIGN PATENT DOCUMENTS

WO    2008031169 A1    3/2008
WO    2012158486 A2    11/2012
(Continued)

OTHER PUBLICATIONS

International Search Report and Written Opinion from PCT Application No. PCT/EP2019/064041, dated Sep. 4, 2019.
(Continued)

*Primary Examiner* — George R Evanisko
(74) *Attorney, Agent, or Firm* — Workman Nydegger

(57) ABSTRACT

A method for deriving information for setting a fitting parameter of a cochlear implant, wherein the cochlear implant includes an electrode array having a plurality of stimulating electrode contacts. The method includes modelling an interface between an electrode contact of the electrode array and a cochlear tissue as a corresponding electrical circuit comprising a resistive component representative of Faradaic resistance at the interface; determining at least an impedance value corresponding to the resistive component; obtaining an indication of a value of a fitting parameter for the electrode contact by mapping the deter-
(Continued)

mined impedance value to a mathematical model relating the fitting parameter to the impedance.

16 Claims, 6 Drawing Sheets

(56) References Cited

U.S. PATENT DOCUMENTS

| | | | |
|---|---|---|---|
| 10,368,762 B2* | 8/2019 | Single | A61N 1/0529 |
| 2011/0288613 A1 | 11/2011 | Smith et al. | |
| 2012/0303094 A1* | 11/2012 | Kals | A61N 1/36039 |
| | | | 607/57 |
| 2015/0265838 A1* | 9/2015 | Kals | A61N 1/36039 |
| | | | 607/57 |
| 2018/0140829 A1* | 5/2018 | Ramos de Miguel, Sr. | |
| | | | A61N 1/37252 |

FOREIGN PATENT DOCUMENTS

| | | |
|---|---|---|
| WO | 2012158486 A3 | 4/2013 |
| WO | 2017100866 A1 | 6/2017 |

OTHER PUBLICATIONS

Duan et al., "A Study of Intra-Cochlear Electrodes and Tissue Interface by Electrochemical Impedance Methods in Vivo", Biomaterials, vol. 25, No. 17, Aug. 1, 2004, pp. 3813-3828.

Mesnildrey et al., "Impedance Measures for a Better Understanding of the Electrical Stimulation of the Inner Ear", Journal of Neural Engineering, vol. 16, No. 1, Jan. 9, 2019, 18 pages.

Peeters et al., "Identification of the Impedance Model of an Implanted Cochlear Prosthesis From Intracochlear Potential Measurements", IEEE Transactions on Biomedical Engineering, Dec. 1, 2004, pp. 2174-2183, vol. 51, No. 12.

Communication pursuant to Article 94(3) EPC from Corresponding European Patent Application No. EP19728384.9, dated Feb. 13, 2024.

* cited by examiner

METHOD FOR DERIVING INFORMATION FOR FITTING A COCHLEAR IMPLANT

FIELD OF THE INVENTION

The present invention is generally related to the field of cochlear implants, audiology and otology.

BACKGROUND OF THE INVENTION

Cochlear implants (CIs) have become the standard of care for treatment of deafness and allow for open-set speech understanding in the majority of implanted patients. Due to enormous success of cochlear implantation more than 500,000 patients have been implanted worldwide.

A cochlear implant (CI) is a surgically implanted neuro-prosthetic device that provides a sense of sound to a person with a moderate to profound sensorineural hearing loss. It replaces the function of the human peripheral hearing organ by direct electrical stimulation of the neurons and the fibres of the cochlear (acoustic) nerve and bypassing the external and middle ear and the dysfunctional inner ear. The brain adapts to the new mode of hearing and can eventually interpret the electric signals as sound and speech. The implant has two main components. The outside component is generally worn behind the ear, but can also be attached to clothing, for example, in case of young children. This component, the sound processor, contains microphones, electronics that include digital signal processing (DSP) chips, battery, and a coil which transmits a signal to the implant across the skin. The inside component, the actual implant, has a coil to receive signals and power, an electronic circuitry and an array of electrodes which is placed into the cochlea and which stimulates the neurons and the fibres of the cochlear nerve.

In order to make cochlear implants work in an optimal way the stimulation parameters for each of the stimulating electrode contacts have to be individually adjusted in each patient. This process of defining the stimulation parameters is called the implant fitting. In particular the stimulation currents corresponding to the sensation thresholds (T-levels) and to the levels of comfortable hearing (C-levels) have to be defined for each electrode contact. The T/C levels are the basic fitting parameters of a cochlear implant.

The thresholds (T levels) and the comfort levels (C levels) of behavioural responses elicited by electrical stimulation with CIs are the result of a superposition of the following phenomena occurring at three different levels:

Level 1: The current spread within the cochlea depending on the cochlear anatomy, electrode positioning and the electrode and tissue impedance Level 2: Neural preservation and excitability of the nerve fibres Level 3: Cortical and behavioural reactions to the excitation patterns elicited in the auditory pathways Given the continuously increasing number of implanted patients, fitting of the implants to the individual patients' needs has become a major burden for professional audiologists. The necessity to define the T/C levels for each particular electrode leads to a labour-intensive process and therefore automatized and/or streamlined fitting procedures have been developed. They are based mostly on electrophysiological measures such as electrically-evoked compound action potentials (ECAP), electrically-evoked auditory brainstem responses (EABR) or electrically-evoked stapedius reflex thresholds (ESRT).

However, all electrophysiological measures (ECAP, EABR, ESRT) are the measures of the phenomena occurring predominantly at level 2, they all show very big variability and are unable to efficiently take into account the anatomical and physiological status at level 1 and 3. Very high variability of the above mentioned measures makes accurate prediction of the behavioural T/C levels only on basis of the above mentioned electrophysiological measures an impossible task. This has already been demonstrated by many researchers and has become the motivation for the development presented in this disclosure.

Hence, there is a need for improvements of the fitting procedure, both in terms of efficiency and accuracy.

SUMMARY OF THE INVENTION

It is an object of embodiments of the present invention to provide for a method for deriving information that allows a more efficient fitting of a cochlear implant.

The above objective is accomplished by the solution according to the present invention.

In a first aspect the invention relates to a method for deriving information for setting a fitting parameter of a cochlear implant, said cochlear implant comprising an electrode array having a plurality of stimulating electrode contacts, the method comprising:

modelling an interface between an electrode contact of said electrode array and a cochlear tissue as a corresponding electrical circuit comprising a resistive component representative of Faradaic resistance at said interface, determining at least an impedance value corresponding to said resistive component, obtaining an indication of a value of a fitting parameter for said electrode contact by mapping said determined impedance value to a mathematical model relating said fitting parameter to said impedance.

The proposed solution indeed allows for obtaining a setting for a fitting parameter value for the electrode contact of the modelled interface, which, when applied to the cochlear implant, leads to an improved fitting of the cochlear implant. It was found by the inventors of the proposed approach that determination of an impedance value corresponding to the resistive component, in particular the Faradaic resistance, of an electrical circuit model representing the interface between an electrode contact of the electrode array and the cochlear tissue yields an excellent basis for performing the cochlear implant fitting.

In a preferred embodiment the method is performed for various electrode contacts of the electrode array, most preferably for all electrode contacts of the array.

In a preferred embodiment also the intracochlear position of the electrode contact in the electrode array is taken into account when obtaining said indication, i.e. which is the position of the electrode contact in the sequence of electrode contacts in the electrode array. In one embodiment the position of the electrode contact is taken into account by considering the distance from the electrode contact to auditory neural tissue.

In embodiments of the invention at least one electrophysiological measure is taken into account when obtaining said indication. The at least one electrophysiological measure is preferably taken from the set comprising {an electrically-evoked compound action potential, an electrically-evoked auditory brainstem response, an electrically-evoked stapedius reflex threshold}.

In one embodiment the at least one electrophysiological measure is the electrically-evoked compound action potential and the rate of stimulation when determining said electrophysiological measure is also taken into account when obtaining said indication.

In embodiments of the invention, in the step of obtaining said indication also a measurement of an electrophysiological cortical response to auditory stimulation is taken into account. The measurement of the cortical response is advantageously one of {a threshold level, a latency of said cortical response, a modulation depth}.

In one embodiment the age at which a patient wearing the cochlear implant, became deaf is taken into account in the step of obtaining the indication. In one embodiment the age is categorized in a prelingual and postlingual class.

In embodiments the etiology of deafness is taken into account in the step of obtaining said indication.

Advantageously, said parameter is a level of comfortable hearing or a hearing sensation threshold level.

In a preferred embodiment the indication is a value of a stimulation current or voltage level corresponding to the value of said parameter.

In embodiments of the invention the corresponding electrical circuit further comprises a capacitive component.

In another aspect the invention relates to a program, executable on a programmable device containing instructions which, when executed, perform the method as set out above.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, wherein like reference numerals refer to like elements in the various figures.

DETAILED DESCRIPTION OF ILLUSTRATIVE EMBODIMENTS

Figure 1:
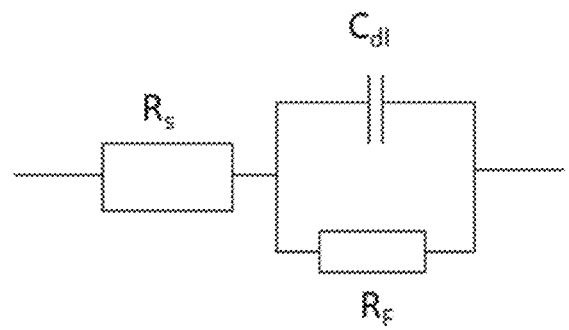
FIG. 1 illustrates a lump element model of the electrode-tissue interface of a cochlear implant.

The present invention will be described with respect to particular embodiments and with reference to certain drawings but the invention is not limited thereto but only by the claims.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

The present invention presents a method for deriving information on the fitting parameters for a cochlear implant based on electrophysiological and physiological parameters that show better mathematical correlation with the behavioural threshold and comfort levels (T-levels and C-levels, respectively) than prior art methods. Since these parameters can be objectively measured and show limited covariance, a metric derived from one or more of these parameters enables an efficient prediction of the behavioural T/C-levels and allows for objective fitting of the cochlear implants without need for any intervention by a trained audiologist or technician.

The complex impedance of the electrode-tissue interface of the cochlear implant can be represented by the lump element model shown in FIG. 1. It comprises a solution resistance $R_s$ in series with a parallel circuit of the double layer capacitor $C_{DL}$ and the resistance $R_F$ corresponding to the Faradaic processes occurring at the electrode-electrolyte interface (i.e. charge transfer or polarization resistance). One recognizes in the equivalent circuit of FIG. 1 also the scheme of a simplified Randles cell. Such a simplified Randles cell can serve as a starting point for other more complex models for representing the electrode-tissue interface.

Figure 2:
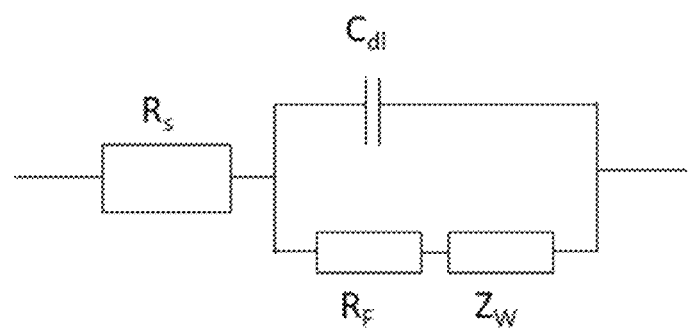
FIG. 2 illustrates a lump element model of the electrode-tissue interface with a Warburg element.

If a semi-infinite diffusion rate determines the charge transfer rates, an additional element (Warburg impedance $Z_W$) is added to the model of the electrode-tissue interface of FIG. 1. The Warburg diffusion element $Z_W$ is a constant phase element (CPE), with a constant phase of 45° (independent of frequency) and with a magnitude inversely proportional to the square root of the frequency. FIG. 2 provides an illustration of an equivalent circuit with Warburg element.

Figure 3:
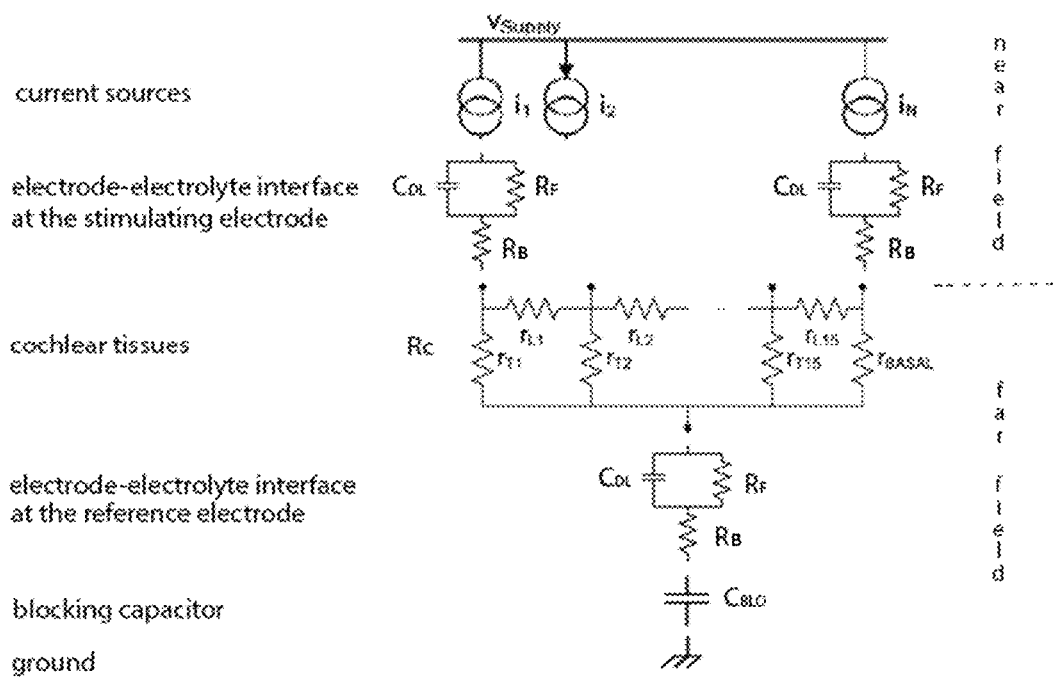
FIG. 3 illustrates an equivalent circuit of the full electrode-electrolyte interface for a cochlear implant electrode array, showing the corresponding circuits of the near-field and the far-field interactions.
Figure 6:
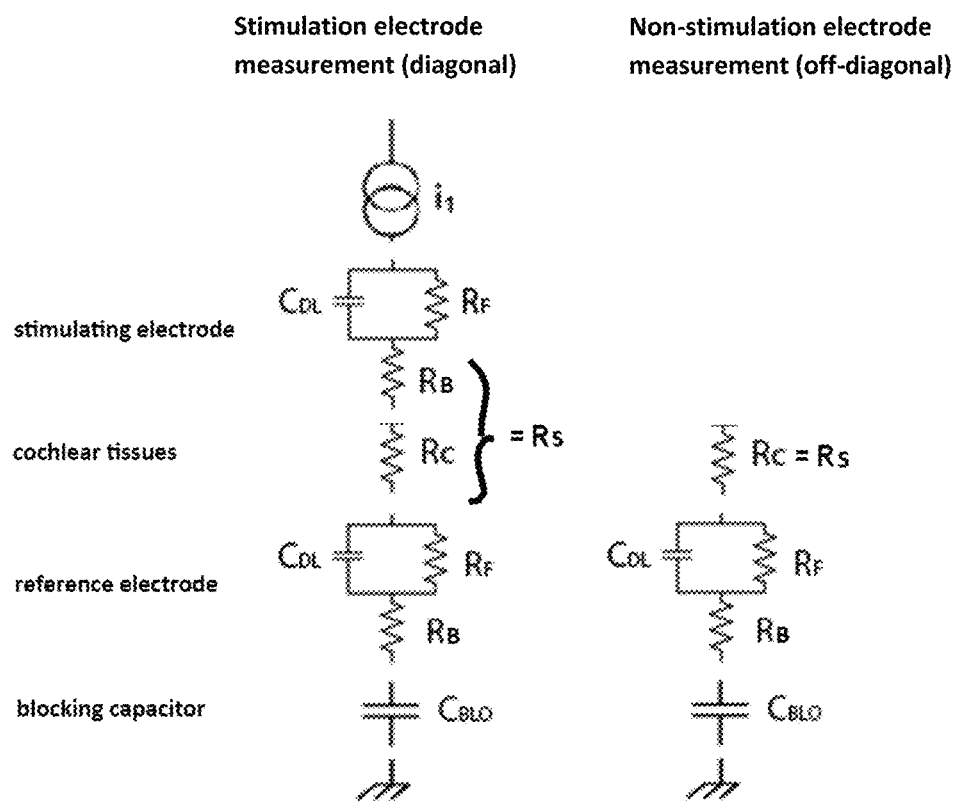
FIG. 6 illustrates corresponding circuits for the electrode-electrolyte impedance and the current paths for the stimulating electrodes (diagonal) and the non-stimulating electrodes (off-diagonal), respectively.

An impedance model of the full interface comprising the electrode-tissue interface and the cochlear tissues, extracochlear reference electrodes, DC blocking capacitor is provided in FIG. 3. The parameters of the impedance model characterize intrinsically different parts of the current path. The double layer capacitance $C_{DL}$, the Faradaic resistance $R_F$ and the so-called bulk resistance $R_B$, which forms a part of the solution resistance $R_s$, model the electrode-tissue interface as already mentioned above. The parameters $C_{DL}$ and $R_F$ are related to the electrochemical processes in the close vicinity of the electrode contact. The double-layer capacitor $C_{DL}$ is capable of storing electrical energy by means of the electrical double layer effect which occurs at the interface between a conductive electrode of the intracochlear array of electrodes and the adjacent liquid electrolyte (i.e. the tissue between the electrode array and the other part of the cochlear implant). As already mentioned, the resistance $R_F$ corresponds to the Faradaic processes occurring at that interface. The bulk resistance $R_B$ contains several components, such as the additional contribution to the impedance due to the current concentration near the electrode contact (which also contributes to the near field effect) and tissue grow around it. The effect of the tissue between the intracochlear electrodes and the extracochlear reference electrodes, i.e. the various transversal resistive components $r_{Ti}$ and longitudinal components $r_{Li}$ depicted in FIG. 3, is lumped together into the single resistive component $R_C$ (FIG. 6), which represents the far-field component. Note that the solution resistance $R_s$ of FIG. 1 and FIG. 2 is equal to the sum of $R_B$ and $R_C$. The capacitance between the extracochlear electrode and the stimulation/recording circuitry (including the serial blocking capacitor between each individual current source and stimulation contact) is in FIG. 3 denoted as $C_{BLO}$.

Figure 4:
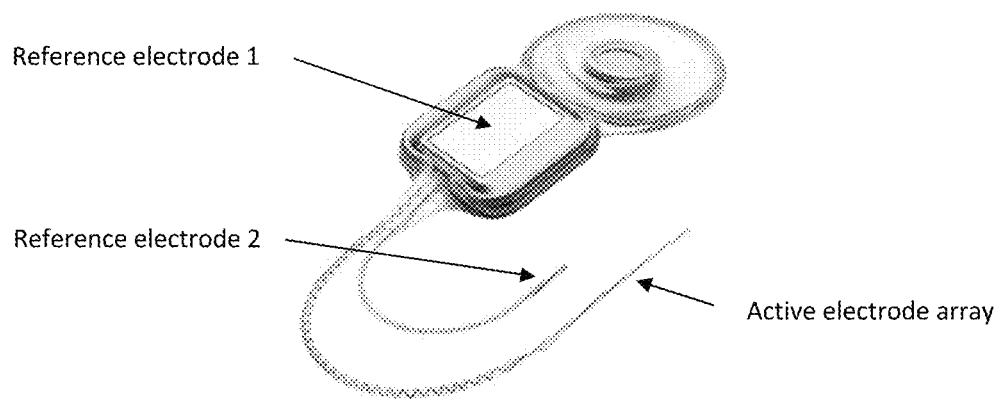
FIG. 4 illustrates a model of a cochlear implant (in this case the Nucleus Profile system) showing both reference electrodes.

FIG. 4 shows two extracochlear reference electrodes for a possible implementation of a cochlear implant. Each of the two extracochlear electrodes has an associated blocking capacitor. During stimulation both extracochlear electrodes are used as reference, simultaneously, hence adding up the effect of the two parallel capacitances $C_{BLO}$. The impedance parameters of the reference electrodes are pragmatically less important than the impedance parameters of the intracochlear electrodes due to their much larger dimensions. Other embodiments of cochlear implants may comprise only one large-size extracochlear reference electrode.

Figure 5:
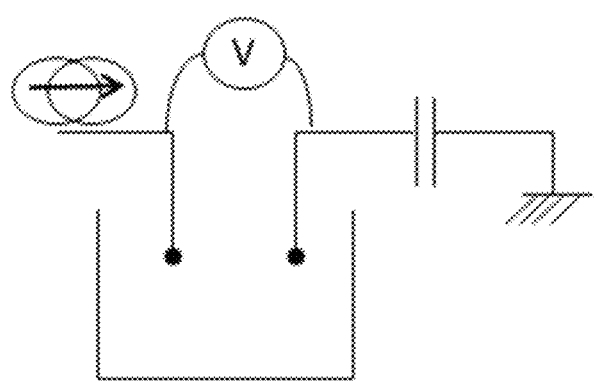
FIG. 5 illustrates a model of the measuring set-up for the diagonal measurements of the voltage response to the current pulses.
Figure 7:
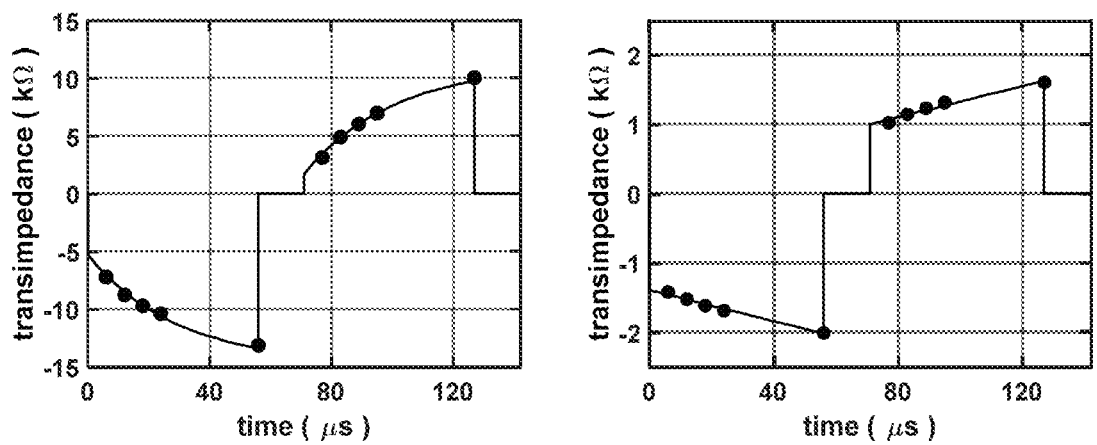
FIG. 7 illustrates a measured and an approximated time response to a stimulating pulse for a diagonal and non-diagonal measurement.

The parameters of the electrical circuit corresponding to the impedance of the electrode-electrolyte interface can be determined by applying the following approach. In some embodiments rectangular bi-phasic pulses are generated between two chosen electrodes in the electrode array. In other embodiments non-rectangular pulses can be used. Any principally charge balanced pulse type can be envisaged for use in the proposed approach, as long as the pulse does not cause charge transfer towards the tissue that might cause tissue damage. The stimulating pulse can be a voltage or a current. One possible scheme of the measurement is shown in FIG. 5. A current pulse is injected at a stimulating electrode and the voltage responses between the stimulating and the reference electrode(s) are measured at the stimulating electrode (diagonal measurement) as well as between all other electrodes and the reference electrode(s) (off-diagonal measurements). In the left hand part of FIG. 6 the relevant current signal path is illustrated for a diagonal measurement, i.e. a measurement at the stimulating electrode, and in the right-hand part for a non-diagonal measurement, i.e. at any of the non-stimulating contacts of the electrode array. Voltage responses to the current pulses are recorded at different moments in time during the monopolar biphasic stimulation pulse. For example, a voltage response measurement may be performed for a biphasic pulse at e.g. 10 instances as illustrated in FIG. 7 (for a diagonal measurement on the left and a non-diagonal measurement on the right): at 6, 12, 18, 24, 56 μs from the leading edge of each of the two pulse phases. In FIG. 7 the left panel shows a typical voltage response measured at the stimulating electrode (diagonal measurement) while the right panel shows the voltage response measured at one of the non-stimulating electrodes of the electrode array (off-diagonal measurements). The dots are the measured data, whereas the solid line represents the model fitting of the signal received in response to the stimulation pulse.

The model parameters can be determined using the following approach. Essentially, the purely resistive components $R_s$ contribute to the instantaneous response, i.e. the step-wise behaviour of the waveform near the leading and trailing edges of the stimulation pulse, as can also be seen from FIG. 7. For diagonal measurements the parallel components $R_F$ and $C_{DL}$ result in an exponentially decaying/growing time response, as no current is assumed to flow through the electrode-tissue interface at electrodes different from the stimulation electrode. The Faradaic resistance $R_F$ corresponds to the amplitude of the exponentially decaying/growing part of the response, whereas the double-layer capacitance $C_{DL}$ is indirectly derived from the time constant $\tau$ via $\tau = C_{DL} R_F$. The implant-related blocking capacitance $C_{BLO}$ gives rise to a linear slope with time during each phase of the stimulation pulse. The blocking capacitance $C_{BLO}$ contributes to both the waveform measured at an electrode different from the intracochlear stimulation electrode (in a non-diagonal measurement) and the waveform at the stimulation electrode itself (diagonal measurement). Because $C_{BLO}$ is common to the recordings at all intracochlear electrodes and because it is the only time-dependent contribution to the off-diagonal measurements, the linear effect of off-diagonal measurements is used to subtract the effect in the diagonal waveforms. This subtraction was already performed in the left panel of FIG. 7. To exclude any effect of the stimulation current, $C_{BLO}$ is preferably determined based on measurements obtained far away from the stimulation electrode. For example, measurements can be used at electrodes at least 18 electrodes away from the stimulating electrode in the array of electrodes.

Figure 8:
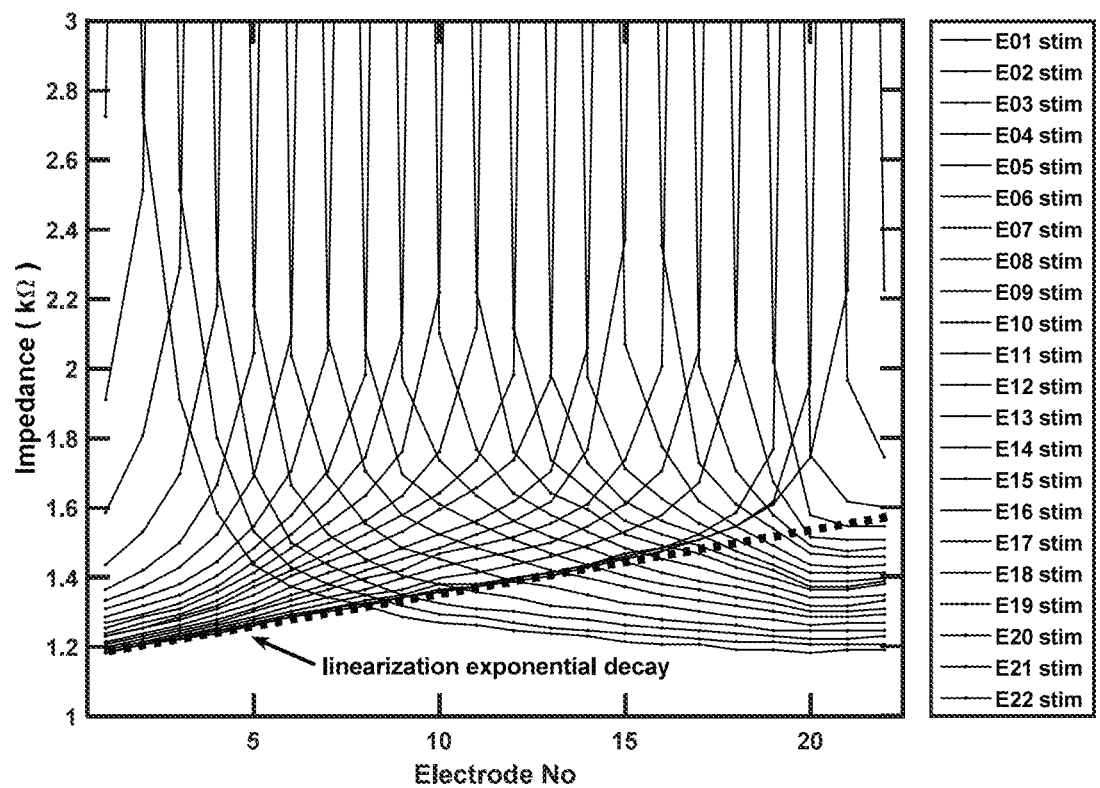
FIG. 8 illustrates a linearization of the exponential decay of the off-diagonal (non-stimulating electrode) voltage amplitudes allowing for calculating the resistance $R_C$.

The waveform fitting allows discriminating between the instantaneous resistive components and the time-dependent capacitive components of the impedance. However, the two resistive contributions $R_B$ and $R_C$ to the solution resistance $R_s$, seen when performing the diagonal measurements, cannot be separated, as the measurement procedure only yields their sum $R_s = R_B + R_C$. To tackle this problem it is assumed that the far field component $R_C$, directly obtained for the waveforms away from the stimulation electrode, can be extrapolated towards the stimulation electrode. The far field component $R_C$ at the stimulation electrode is thus obtained by fitting the field spread $R_C$ from the non-stimulating measurements to a double-sided exponential on a linear function, with the constraint that basal and apical fitting meet each other at the stimulation electrode. $R_s$ from the waveform fitting at the stimulation electrode and $R_C$ from extrapolating the non-stimulating field spread then also yield the bulk resistance $R_B$ at the stimulation electrode. FIG. 8 shows the linearization of the exponential decay of the off-diagonal (non-stimulating electrode) voltage amplitudes allowing for calculating of the $R_C$.

It was found that one particular component of the complex impedance model presented above very accurately correlates with the behavioural T/C levels, namely the resistive component $R_F$ corresponding to the Faradaic processes occurring at the electrode-electrolyte interface. This finding clearly indicates the importance of taking into account the near-field effects during simulations for fitting cochlear implants. This resistive Faradaic component $R_F$ is the most preferred correlating single parameter of the predictive metric which allows for objective calculation of the behavioural T/C-levels.

Figure 9:
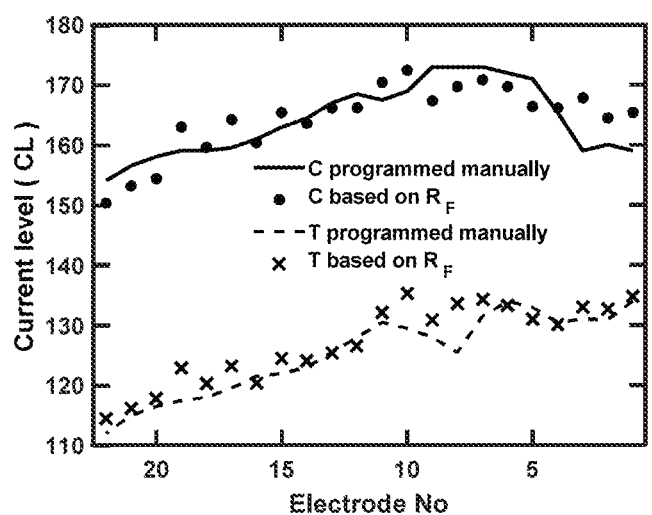
FIG. 9 illustrates a comparison of measured and predicted T/C levels for a case where only the Faradaic resistance $R_F$ is considered.

For certain patients it is sufficient to use only this resistive component $R_F$ as a basis for prediction of the T/C-levels in order to obtain satisfactory results. FIG. 9 shows that the median result of the estimation of the T/C fitting parameters (measured behaviourally) over the various electrodes of the array in a number of patients indeed almost exactly agrees with the T/C levels calculated on basis of the correlation with the resistive Faradaic component $R_F$. The upper curves in FIG. 9 show the differences found for the C levels and the lower curves for the T levels.

Figure 10:
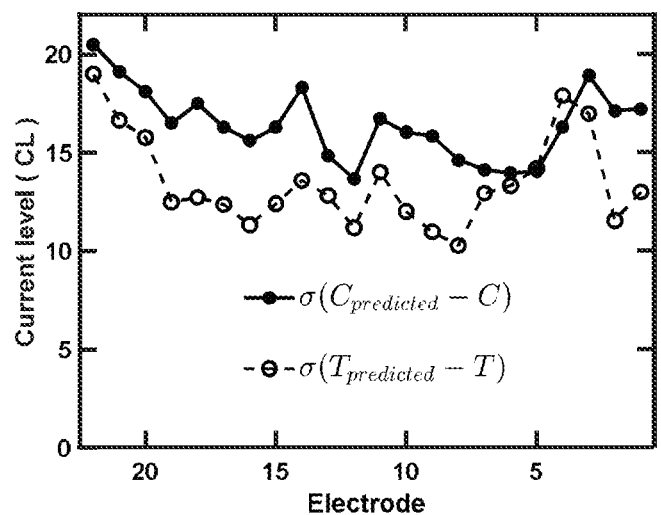
FIG. 10 illustrates the differences still being found in some cases between the T and C levels predicted upon the $R_F$ and the T and C levels measured behaviourally.

Although in certain cases the agreement between the behaviourally measured T/C-levels and the predictions calculated on basis of the resistive component $R_F$ alone is excellent, it is found that in other cases, with other patients, the standard deviation σ of the differences calculated for individual contacts is still large, as illustrated in FIG. 10. The upper curve shows the standard deviation for the C levels and the lower curve for T levels. Hence, in order to decrease the variability of the differences between the behaviourally measured T/C levels and the predictions calculated on basis of the resistive component additional parameters have to be added to the metric equation.

Figure 11:
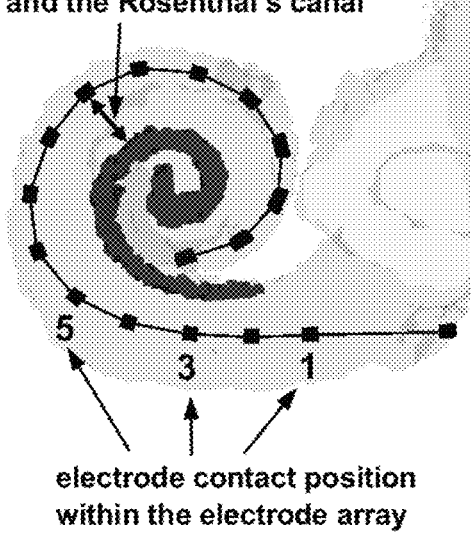
FIG. 11 illustrates the distance between the electrode contacts and the Rosenthal's canal in which the stimulated neurons (spiral ganglion cells) are located.

In a mathematical model correlations between the measured impedance values and the predicted T/C levels are significantly better for the electrode contact lying closer to the excitable neural structures contained inside the modiolus. The modiolus is the central part of the cochlea containing the spirally organized neurons of the auditory nerve (spiral ganglion cells). These cells are located in a bony canal called the Rosenthal's canal extending along the medial wall of the cochlear fluid-filled spaces, as illustrated in FIG. 11. It is generally assumed that decreasing the distance from a stimulating contact to the Rosenthal's canal results in lower monopolar current thresholds for neural excitation. When the various intracochlear electrode contacts along the array are considered, a significant correlation in the mathematical model can be demonstrated for the actually measured distances.

The required calculations in the mathematical model can be performed relying on e.g. a set of behavioural T/C levels, intraoperative electrically-evoked compound action potentials (ECAP) thresholds and cone-beam computed tomography (CBCT) scans. The patient specific anatomical information is available since CBCT is widely used in cochlear implant patients: preoperatively for visualization of the surgical anatomy and postoperatively in order to evaluate the depth and quality of electrode insertion. To overcome the drawback of poor soft-tissue delineation in CBCT, the location of Rosenthal's canal can be estimated by non-rigidly co-registering a micro-tomography and in-vivo CBCT scans.

Figure 12:
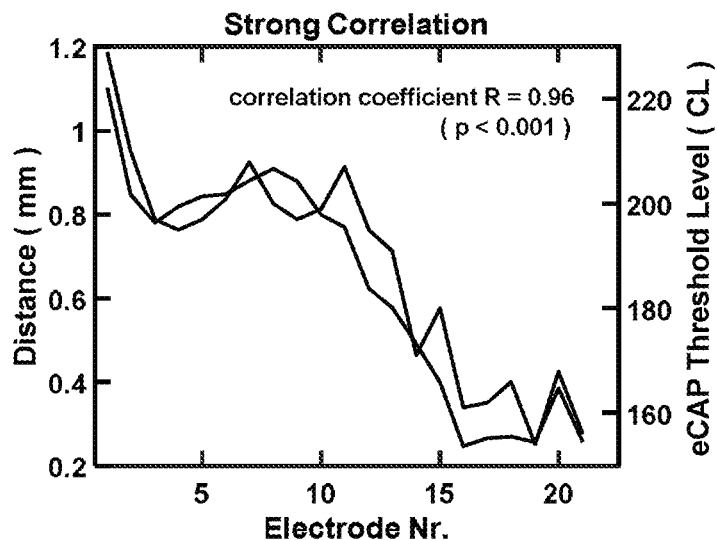
FIG. 12 illustrates the significant agreement between the intraoperative eCAP measurements derived from the electrophysiological auto-NRT responses and the distance to the Rosenthal's canal.

In the mathematical model strong positive correlations are found between the distance to Rosenthal's canal and the T/C levels and between the distance to the Rosenthal's canal and ECAP thresholds. Placement closer to the Rosenthal's canal results in lower currents necessary for evoking a neural response. FIG. 12 provides an illustration of the agreement between the intraoperative eCAP measurements derived from the electrophysiological Auto-Neural Response Telemetry (Auto-NRT) responses and the distance to the Rosenthal's canal. In the case depicted in FIG. 12 the calculated Pearson correlation coefficient is 0.96 ($p<0.001$).

Prediction of the T/C-levels is also possible on basis of neural responses to the voltage gradients created in the vicinity of the stimulating electrodes. Electrophysiological parameters like the electrically-evoked compound action potentials (ECAP), electrically-evoked auditory brainstem responses (EABR) or electrically-evoked stapedius reflex thresholds (ESRT) can serve as basis.

It is however well known in the art that only weak to moderate correlations between these parameters and the behavioural T/C levels are found. Hence, the fact that these correlations are only weak to moderate renders these parameters unsuitable to serve as sole basis to perform predictions of the T/C levels. The ESRT seems to give best results, but in general no major differences in the predictive value of these parameters can be demonstrated.

All the above mentioned electrophysiological parameters also co-variate (i.e. they are intercorrelated). This is caused by the fact that they all characterize the excitability of the neural structures lying in the vicinity of the stimulating electrodes. Therefore also a metric created as a combination of solely these parameters does not substantially improve the prediction accuracy.

However, adding any of these parameters to the metric containing the objectively measured parameters of the previously described embodiments significantly improves the quality of the prediction. This is due to the fact that phenomena occurring at the level of the preservation and the physiological status of the neurons and the nerve fibres, are independent of the anatomy of the cochlea, position of the electrode, etc. The parameters measured at the above-mentioned level 1 explain most of the variability of the T/C-levels, while adding the parameters related to neural preservation and excitability of the nerve fibres to the mathematical model helps to improve the prediction quality as they explain additional sources of variability.

In further embodiments of the proposed method also cortical and behavioural reactions to the excitation patterns elicited in the auditory pathways can be taken into account.

At the cortical level the cognitive aspects play an important role and there is large personal variability present. An important parameter in the functional variability of the central auditory pathways is related to the development of the pathways in function of the age of the patient and the previous auditory experience.

Figure 13:
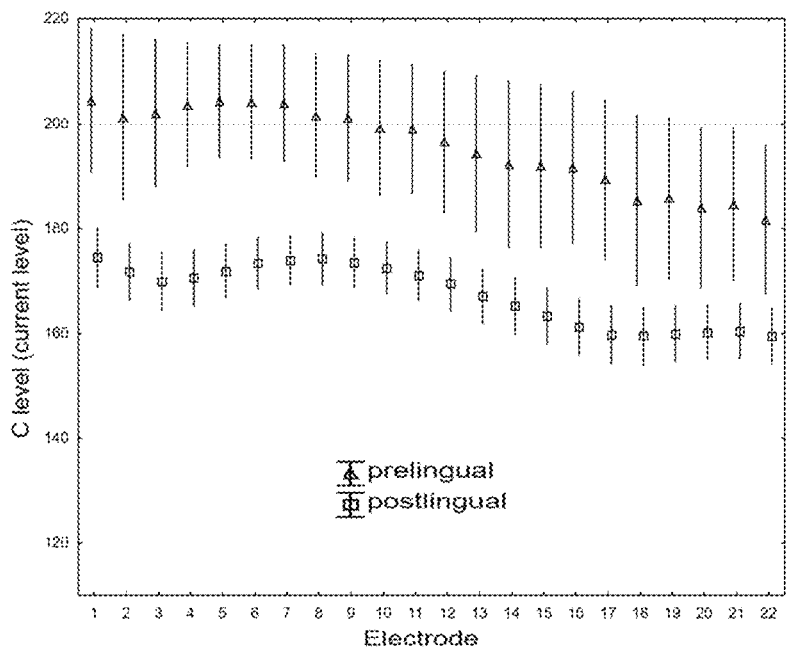
FIG. 13 illustrates the average values of the C levels during the fifth fitting session for both prelingually and postlingually implanted patients.

Significant differences in the behavioural T/C levels can be demonstrated between patients with or without the auditory experience. FIG. 13 shows the average values of the T/C-levels during the fifth fitting session for both prelingually and postlingually implanted patients. Especially for the C levels there exist significant differences between the pre- and postlingual patients with prelingual patients showing higher C levels.

In certain embodiments the etiology of deafness is taken into account. Certain etiologies (e.g. post-inflammatory cochlear ossification) can result in a partial degeneration of the neurons and the nerve fibres of the auditory branch of the cochleovestibular nerve. This may lead to decreased responsivity of the nerve, increased T/C levels, decreased dynamic range (i.e. the difference between the T and the C levels) or signs of neural adaptation. In these cases the electrophysiological measurements of the level 2 show characteristic abnormalities that have to be considered in the prediction model of the behavioural T/C levels. Also MRI imaging can show decreased diameter of the auditory branch of the cochleovestibular nerve in specific patients that should also be taken into account by the prediction model.

Another possibility to characterize the cognitive aspects of hearing is to measure the cortical responses to auditory stimulation. One or a combination of the following cortical responses can be used:

Thresholds of the human scalp-recorded event-related cortical responses to the auditory signals Latencies of the human scalp-recorded event-related cortical responses Modulation transfer functions of the frequency following responses Phenomena occurring at this level are once again independent of the cochlear anatomy, electrode positioning or the physiological status of the peripheral nerve fibres. Adding them to the predictive metric in the mathematical model once again helps to improve the prediction quality by explaining additional sources of variability.

Many metrics can be defined in the mathematical model, whereby some or all of the above-described parameters are combined to allow efficient prediction of the behavioural T/C levels. The metric can be calculated using e.g. the deterministic multiple regression or principal components methods, however the use of non-deterministic artificial intelligence algorithms can additionally improve the quality of prediction.

Artificial intelligence (AI) techniques, which encompass machine learning, use computer algorithms to learn from data, to help identify patterns in data and make predictions. A key feature of artificial intelligence techniques and machine learning is their potential to analyse large and complex data structures and to create prediction models. In this case AI can be used for making predictions for the T/C levels and improving the fitting outcomes. For large amounts of input parameters showing multiple interactions the AI approach is most efficient in obtaining the relative weights of each of the parameters in function of the values of other parameters in the equation. The initial model (metric) is created on basis of the data (input parameters and the T/C-level outcomes) of a number of patients. The metric created on basis of these data is used to predict the behavioural T/C-levels in new patients (not being the part of the model).

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or

The invention claimed is:

1. A method for deriving information for setting a fitting parameter of a cochlear implant, said cochlear implant comprising an electrode array having a plurality of stimulating electrode contacts, the method comprising:
generating a model of an interface between an electrode contact of said electrode array and a cochlear tissue by modelling the interface as a corresponding electrical circuit comprising a resistive component representative of Faradaic resistance at said interface,
applying an electrical pulse to one of said stimulating electrode contacts of said electrode array and measuring a voltage response to said pulse,
determining a value of an impedance corresponding to said resistive component from said measured voltage response,
determining the Faradaic resistance component from the impedance,
obtaining an indication of a value of the fitting parameter for said electrode contact to which the electrical pulse was applied using the Faradaic resistance component, and by mapping said determined impedance value to a mathematical model relating said fitting parameter to said impedance,
wherein the Faradaic resistance corresponds to an amplitude of an exponentially decaying/growing part of the voltage response at said stimulating electrode.

2. The method for deriving information for fitting as in claim 1, wherein in said obtaining said indication also the position of said electrode contact to which the electrical pulse was applied in said electrode array is taken into account.

3. The method for deriving information for fitting as in claim 2, wherein said position of said electrode contact to which the electrical pulse was applied is taken into account by considering the distance from said electrode contact to auditory neural tissue.

4. The method for deriving information for fitting as in claim 1, wherein at least one electrophysiological measure is taken into account when obtaining said indication.

5. The method for deriving information for fitting as in claim 4, wherein said at least one electrophysiological measure is taken from:
an electrically-evoked compound action potential,
an electrically-evoked auditory brainstem response,
an electrically-evoked stapedius reflex threshold.

6. The method for deriving information for fitting as in claim 5, wherein said at least one electrophysiological measure is said electrically-evoked compound action potential and
wherein also the rate of stimulation when determining said electrophysiological measure is taken into account when obtaining said indication.

7. The method for deriving information for fitting as in claim 1, wherein in said step of obtaining said indication also a measurement of an electrophysiological cortical response to auditory stimulation is taken into account.

8. The method for deriving information for fitting as in claim 7, wherein said measurement of said cortical response is one of:
a threshold level,
a latency of said cortical response,
a modulation depth.

9. The method for deriving information for fitting as in claim 1, wherein in said step of obtaining said indication the age at which a patient wearing said cochlear implant, became deaf is taken into account.

10. The method for deriving information for fitting as in claim 9, wherein said age is categorized in a prelingual and post lingual class.

11. The method for deriving information for fitting as in claim 1, wherein in said step of obtaining said indication the etiology of deafness is taken into account.

12. The method for deriving information for fitting as in claim 1, wherein said fitting parameter is a level of comfortable hearing or a hearing sensation threshold level.

13. The method for deriving information for fitting as in claim 1, wherein said indication is a value of a stimulation current or voltage level corresponding to said value of said parameter.

14. The method for deriving information for fitting as in claim 1, wherein said corresponding electrical circuit further comprises a capacitive component.

15. A non-transitory computer readable medium comprising program instructions adapted to perform the method as in claim 1 when executed on a programmable device.

16. A method for deriving information for setting a fitting parameter of a cochlear implant, said cochlear implant comprising an electrode array having a plurality of stimulating electrode contacts, the method comprising:
generating a model of an interface between an electrode contact of said electrode array and a cochlear tissue by modelling the interface as a corresponding electrical circuit comprising a resistive component representative of Faradaic resistance at said interface,
applying an electrical pulse to one of said stimulating electrode contacts of said electrode array and measuring a voltage response to said pulse,
determining a value of an impedance corresponding to said resistive component representative of only Faradaic resistance from said measured voltage response,
determining the Faradaic resistance component from the impedance,
obtaining an indication of a value of the fitting parameter for said electrode contact to which the electrical pulse was applied using the Faradaic resistance component, and by mapping said determined impedance value to a mathematical model relating said fitting parameter to said impedance.

* * * * *